US00PP37469P3

(12) United States Plant Patent
Saul

(10) Patent No.: US PP37,469 P3
(45) Date of Patent: Jun. 9, 2026

(54) ***RUDBECKIA* PLANT NAMED 'Dahlonega'**

(50) Latin Name: *Rudbeckia fulgida var. sullivantii*
Varietal Denomination: Dahlonega

(71) Applicant: Richard Saul, Cleveland, GA (US)

(72) Inventor: Richard Saul, Cleveland, GA (US)

(73) Assignee: SAUL TRADEMARKS.COM, Cleveland, GA (US)

( * ) Notice: Subject to any disclaimer, the term of this patent is extended or adjusted under 35 U.S.C. 154(b) by 0 days.

(21) Appl. No.: 19/204,564

(22) Filed: May 11, 2025

(65) Prior Publication Data

US 2025/0374842 P1 Dec. 4, 2025

Related U.S. Application Data

(60) Provisional application No. 63/653,417, filed on May 30, 2024.

(51) Int. Cl.
*A01H 5/02* (2018.01)
*A01H 6/14* (2018.01)

(52) U.S. Cl.
USPC ..... Plt./474
CPC ..... *A01H 6/14* (2018.05); *A01H 5/02* (2013.01)

(58) Field of Classification Search
USPC ..... Plt./474
See application file for complete search history.

(56) References Cited

PUBLICATIONS https://provenwinnersdirect.com/products/mega-millions-black-eyed-susan?srsltid=AfmBOopRdp0OVksj_7c9t4T_NWVoAl1Tv_QK-0_t4KEBVP_2n-BY2jW0 p. 3 (Year: 2023).*
https://www.provenwinners.com/plants/rudbeckia/mega-millions-black-eyed-susan-rudbeckia-fulgida Nexus between 'Dahlonega' and 'Mega Millions' p. 1 (Year: 2025).*

* cited by examiner

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Rudbeckia* plant named 'Dahlonega', characterized by its tall and upright plant habit; vigorous growth habit; freely branching habit; sturdy flowering stems; numerous large single-type inflorescences with golden yellow-colored ray florets with dark brown-colored disc florets; and relative resistance to *Septoria* Leafspot.

2 Drawing Sheets

CLOSELY-RELATED APPLICATIONS

Figure 1:
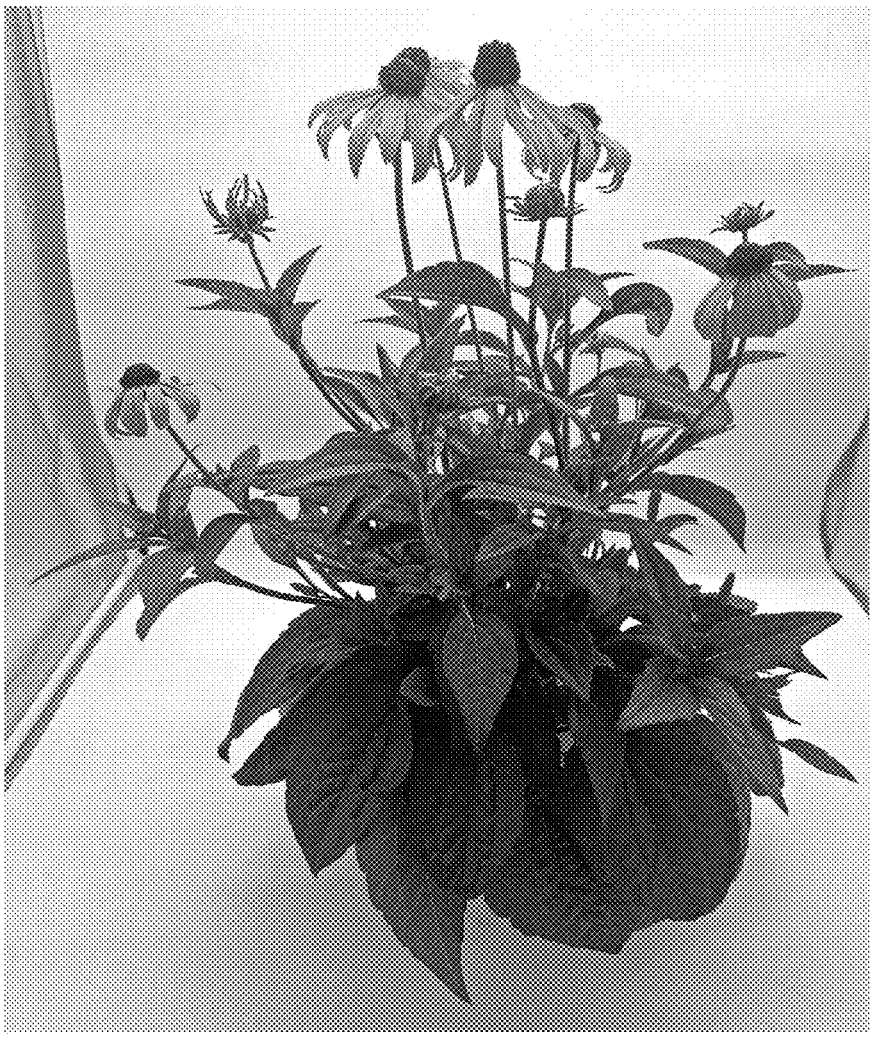

A provisional U.S. Patent application was filed by the Inventor/Applicant, Richard Saul, on May 30, 2024, serial number 63/653,417. Priority is claimed to this application.

Botanical designation: *Rudbeckia fulgida* var. *sullivantii*.

Cultivar denomination: 'DAHLONEGA'.

BACKGROUND OF THE INVENTION

The present invention relates to a new and distinct cultivar of *Rudbeckia* plant, botanically known as *Rudbeckia fulgida* var. *sullivantii*, and hereinafter referred to by the name 'Dahlonega'.

The new *Rudbeckia* plant is a product of a planned breeding program conducted by the Inventor in Dahlonega, Georgia. The objective of the breeding program is to develop new vigorous and freely flowering *Rudbeckia* plants with large inflorescences with unique and intense ray floret coloration.

The new *Rudbeckia* plant originated from an open-pollination in Dahlonega, Georgia of *Rudbeckia fulgida* var. *sullivantii* 'Goldsturm', not patented, as the female, or seed, parent with an unknown proprietary selection of *Rudbeckia fulgida* var. *sullivantii*, as the male, or pollen, parent. The new *Rudbeckia* plant was discovered and selected by the Inventor as a single flowering plant from within the progeny of the stated open-pollination grown in a controlled greenhouse environment in Dahlonega, Georgia in August, 2016.

Asexual reproduction of the new *Rudbeckia* plant by in vitro meristem culture in a controlled environment in Dahlonega, Georgia since April, 2018 has shown that the unique features of this new *Rudbeckia* plant are stable and reproduced true to type in successive generations.

SUMMARY OF THE INVENTION

Plants of the new *Rudbeckia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dahlonega'. These characteristics in combination distinguish 'Dahlonega' as a new and distinct *Rudbeckia* plant:

1. Tall and upright plant habit.
2. Vigorous growth habit.
3. Freely branching habit.

4. Sturdy flowering stems.
5. Numerous large single-type inflorescences with golden yellow-colored ray florets with dark brown-colored disc florets.
6. Relatively resistant to *Septoria* Leafspot.

Plants of the new *Rudbeckia* can be compared to plants of the female parent, 'Goldsturm'. Plants of the new *Rudbeckia* differ primarily from plants of 'Goldsturm' in the following characteristics:

1. Plants of the new *Rudbeckia* are taller and more vigorous than plants of 'Goldsturm'.
2. Plants of the new *Rudbeckia* are more freely flowering than plants of 'Goldsturm'.
3. Plants of the new *Rudbeckia* are more resistant to *Septoria* Leafspot than plants of 'Goldsturm'.

Plants of the new *Rudbeckia* can be compared to plants of *Rudbeckia fulgida* var. *sullivantii* 'Goldblitz', not patented. In side-by-side comparisons, plants of the new *Rudbeckia* differ primarily from plants of 'Goldblitz' in the following characteristics:

1. Plants of the new *Rudbeckia* are taller and more vigorous than plants of 'Goldblitz'.
2. Plants of the new *Rudbeckia* are more freely flowering than plants of 'Goldblitz'.
3. Plants of the new *Rudbeckia* are more resistant to *Septoria* Leafspot than plants of 'Goldblitz'.

BRIEF DESCRIPTION OF THE PHOTOGRAPHS

The accompanying photographs illustrate the overall appearance of the new *Rudbeckia* plant showing the colors as true as it is reasonably possible to obtain in colored reproductions of this type. Colors in the photographs may differ slightly from the color values cited in the detailed botanical description which accurately describe the colors of the new *Rudbeckia* plant.

The photograph on the first sheet (FIG. 1) is a side perspective view of a typical flowering plant of 'Dahlonega' grown in a container.

Figure 2:
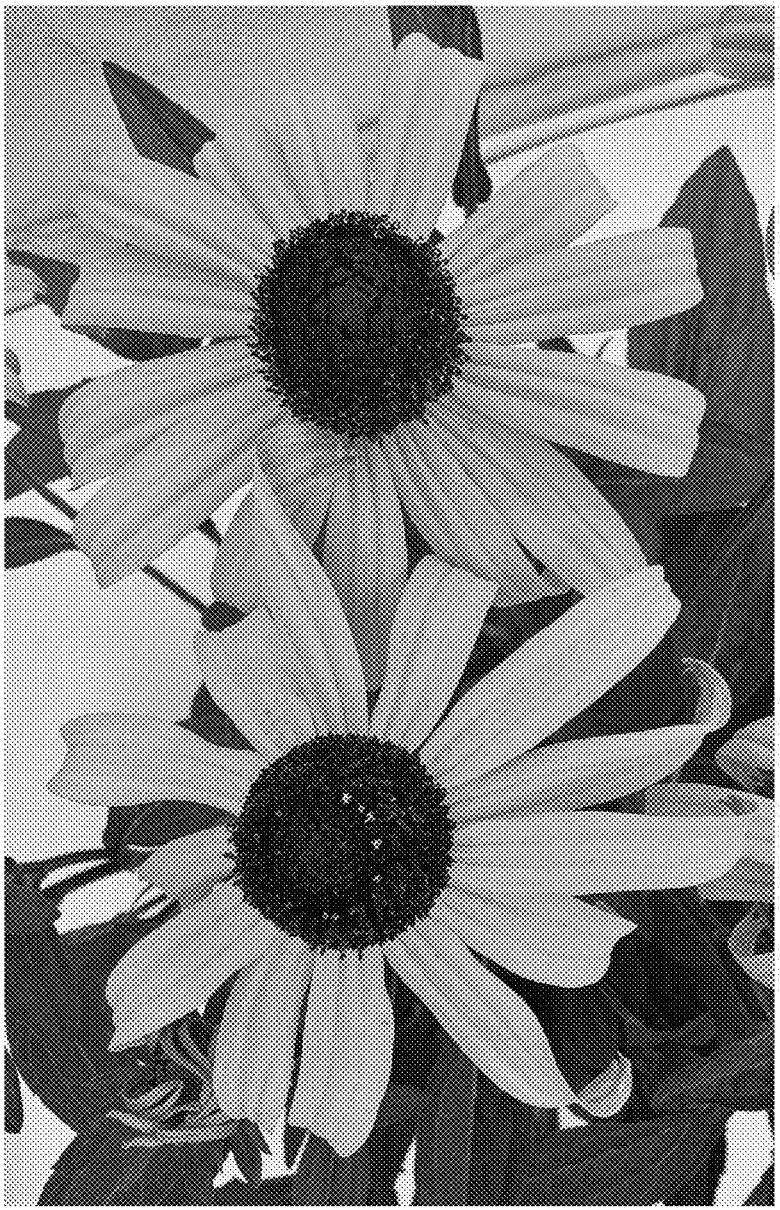

The photograph on the second sheet (FIG. 2) is a close-up view of typical inflorescences of 'Dahlonega'.

DETAILED BOTANICAL DESCRIPTION

The aforementioned photographs and following observations and measurements describe plants grown during the late winter and spring in one-gallon containers in a glass-covered greenhouse in Carleton, Michigan and under cultural practices typically used in commercial *Rudbeckia* production. During the production of the plants, day and night temperatures ranged from 20° C. to 22° C. Plants were 21 weeks old when the photographs and description were taken. In the following description, color references are made to The Royal Horticultural Society Colour Chart, 2015 Edition, except where general terms of ordinary dictionary significance are used.

Botanical classification: *Rudbeckia fulgida* var. *sullivantii* 'Dahlonega'.

Parentage:

*Female parent.*—*Rudbeckia fulgida* var. *sullivantii* 'Goldsturm', not patented.

*Male parent.*—Unknown proprietary selection of *Rudbeckia fulgida* var. *sullivantii*, not patented.

Propagation:

*Type.*—By in vitro meristem culture.

*Time to initiate roots, summer.*—About two weeks at temperatures day temperatures about 29° C. and night temperatures about 18° C.

*Time to produce a rooted young plant, summer.*—About four weeks at temperatures day temperatures about 29° C. and night temperatures about 18° C.

*Root description.*—Medium in thickness, fleshy; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant form and growth habit.*—Herbaceous perennial; tall and upright plant habit; obovate in overall shape; freely basal branching habit with about seven to nine primary lateral branches per plant with secondary lateral branches potentially developing at every node; relatively vigorous growth habit and moderate to rapid growth rate.

*Plant height.*—About 36.5 cm.

*Plant diameter or spread.*—About 42 cm.

*Lateral branches.*—Length: About 27.5 cm. Diameter: About 7.5 mm. Internode length: About 2.5 cm. Aspect: Erect to about 30° from vertical. Strength: Sturdy, becoming rigid with development. Texture: Pubescent, strigose; longitudinally ridged. Color: Close to 144A with longitudinal lines, close to 187A.

Leaf description:

*Basal and cauline leaves.*—Arrangement: Alternate, simple. Length, largest leaves: About 13.5 cm. Width, largest leaves: About 7.25 cm. Shape: Ovate. Apex: Narrowly acute and mucronate. Base: Obtuse. Margin: Shallowly and coarsely dentate or crenate; slightly undulate. Texture and luster, upper surface: Rough, glabrous; slightly glossy. Texture and luster, lower surface: Rough, glabrous; matte. Venation pattern: Pinnate. Color: Developing leaves, upper surface: Close to NN137A. Developing leaves, lower surface: Close to between 138A and 137B. Fully expanded leaves, upper surface: Close to between NN137A and N189A; venation, close to 146A. Fully expanded leaves, lower surface: Close to 147B; venation, close to 146B.

*Petioles, basal and cauline leaves.*—Length, largest leaves: Variable, about 6 cm to 11 cm. Diameter, largest leaves: About 3 mm by 6 mm. Texture, upper and lower surfaces: Mostly smooth and glabrous with sparse pubescence along petiole edges. Color, upper surface: Close to NN137A; midvein, close to 147C. Color, lower surface: Close to 147A to 147B; midvein, close to 146B.

Inflorescence description:

*Appearance.*—Single type inflorescences with ray and disc florets arranged on a capitulum; inflorescences positioned upright above the foliar plane on upright to outwardly slanting and strong peduncles.

*Flowering habit.*—Freely flowering habit with about 25 to 30 developing and fully developed inflorescences per plant at one time.

*Fragrance.*—Not detected.

*Time to flower.*—Plants flower continuously from late spring throughout the summer in an outdoor nursery in Michigan.

*Inflorescence longevity*.—Depending on temperatures, inflorescences last for about two or three weeks on the plant; inflorescences persistent.

*Inflorescence buds, before showing ray floret color*.—Height: About 5 mm. Diameter: About 7.5 mm. Shape: Oblate with a flattened top. Color: Immature involucral bracts, close to 146A.

*Inflorescence size*.—Diameter: Large about 11.25 cm. Depth (height): About 2.25 cm. Disc diameter: About 2 cm.

*Receptacles*.—Height: About 8 mm. Diameter: About 8 mm. Shape: Conical. Color: Close to 154D.

*Ray florets*.—Quantity and arrangement: About 13 to 18 arranged in a single whorl. Length: About 5.5 cm. Width: About 1.25 cm. Shape: Narrowly oblong. Apex: Emarginate to praemorse; individual tips are narrowly acute. Base: Narrowly cuneate with a short basal corolla tube. Margin: Entire; slightly undulate. Texture and luster, upper surface: Smooth, glabrous; moderately velvety; matte. Texture and luster, lower surface: Smooth, glabrous; slightly glossy; venation prominent. Aspect: Initially upright to horizontal and reflexing with development. Color: When opening, upper surface: Close to 14A. When opening, lower surface: Close to N144A. Fully opened, upper surface: Close to 17A to 17B; at the base, close to 155D; venation, similar to lamina colors; colors do not fade with subsequent development. Fully opened, lower surface: Close to 13A to 13B; venation, close to 144A; color does not fade with subsequent development.

*Disc florets*.—Quantity and arrangement: About 325 per inflorescence, arranged spirally at the center of the inflorescence. Length: About 6 mm. Diameter: About 2 mm. Shape: Tubular; distal 10% free, not fused. Apex: Acute. Base: Fused. Margin, free-part: Entire. Texture and luster, inner and outer surfaces: Smooth, glabrous; moderately glossy. Color, inner and outer surfaces: Apex and mid-section: Close to 166A. Base: Close to 144C.

*Receptacle spines*.—To date, receptacle spine development has not been observed on plants of the new *Rudbeckia*.

*Involucral bracts*.—Quantity per inflorescence: About 18 to 20 arranged in two whorls; fused at the base. Length, outer whorl: About 1.3 cm to 1.6 cm. Width, outer whorl: About 4 mm. Length, inner whorl: About 9 mm to 11 mm. Width, inner whorl: About 3 mm. Shape: Lanceolate to linear; slightly reflexed. Apex: Acute. Margin: Entire. Texture and luster, upper and lower surfaces: Smooth, glabrous; matte. Color, upper surface: Distally, close to NN137A and proximally, close to NN137B. Color, lower surface: Distally, close to NN137A and proximally, close to 138A.

*Peduncles*.—Length: Variable, about 9 cm to 12 cm. Diameter: About 3 cm. Strength: Sturdy. Aspect: Mostly upright. Texture: Moderately pubescent; strigose. Color: Close to 146A.

*Reproductive organs* (*present on disc florets only*).—Androecium: Quantity per floret: Five. Filament length: About 1.5 mm. Filament color: Close to 155D. Anther length: About 1 mm. Anther shape: Linear. Anther color: Close to 165A. Pollen amount: None observed. Gynoecium: Quantity per floret: One. Pistil length: About 1.5 mm. Stigma shape: Linear, decurrent. Stigma color: Close to 12A. Style length: About 1 mm. Style color: Close to 154D. Ovary color: Close to 145A. Seeds and fruits: To date, seed and fruit development have not been observed on plants of the new *Rudbeckia*.

Pathogen & pest resistance: To date, plants of the new *Rudbeckia* have been observed to be relatively resistant to *Septoria* Leafspot (*Septoria rudbeckiae*). Plants of the new *Rudbeckia* have not been shown to be resistant to pests and other pathogens common to *Rudbeckia* plants.

Garden performance: Plants of the new *Rudbeckia* have been observed to tolerate rain and wind. Plants of the new *Rudbeckia* have been observed to tolerate temperatures ranging from about 15° C. to 38° C.

It is claimed:

1. A new and distinct *Rudbeckia* plant named 'Dahlonega' as herein illustrated and described.

* * * * *